United States Patent [19]
Chen et al.

[11] Patent Number: 5,834,394
[45] Date of Patent: Nov. 10, 1998

[54] FLUIDIZED-BED CATALYST FOR PROPYLENE AMMOXIDATION TO ACRYLONITRILE

[75] Inventors: Xin Chen; Lianghua Wu, both of Shanghai, China

[73] Assignees: China-Petro-Chemical Corporation; Shanghai Research Institute of Petrochemical Engineering Sinopec, both of China

[21] Appl. No.: 904,914

[22] Filed: Aug. 1, 1997

[30] Foreign Application Priority Data

| Aug. 6, 1996 | [CN] | China | 96116453.0 |
| Aug. 6, 1996 | [CN] | China | 96116454.9 |
| Aug. 6, 1996 | [CN] | China | 96116455.7 |

[51] Int. Cl.$^6$ .............. B01J 23/00; B01J 23/10
[52] U.S. Cl. .......... 502/302; 502/305; 502/306; 502/311; 502/312; 502/319; 502/320
[58] Field of Search .................. 502/305, 306, 502/311, 312, 319, 320, 302

[56] References Cited

U.S. PATENT DOCUMENTS

| 4,443,556 | 4/1984 | Aoki et al. | 502/212 |
| 4,978,765 | 12/1990 | Sasaki et al. | 558/324 |
| 5,134,105 | 7/1992 | Paparizos et al. | 502/205 |
| 5,212,137 | 5/1993 | Suresh et al. | 502/212 |
| 5,223,469 | 6/1993 | Chen et al. | 502/205 |
| 5,235,088 | 8/1993 | Paparizos et al. | 558/324 |

*Primary Examiner*—Elizabeth D. Wood
*Attorney, Agent, or Firm*—Pennie & Edmonds LLP

[57] ABSTRACT

A catalyst for ammoxidation of propylene to acrylonitrile, comprising a) a catalytic composition represented by the following general formula:

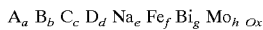

$$A_a B_b C_c D_d Na_e Fe_f Bi_g Mo_h O_x$$

wherein
A represents K, Rb, Cs, Tl, or a mixture thereof,
B represents Mn, Mg, Sr, Ca, Ba, or a mixture thereof,
C represents P, As, B, Sb, Cr, W, V, or a mixture thereof, and
D represents one of the following groups:
  1) Ni alone,
  2) Co alone,
  3) Ni and one selected from Li, Pr, Nd, or a mixture thereof,
  4) Co and one selected from Li, Pr, Nd, or a mixture thereof,
  5) Ni, Co and one selected from Li, Pr, Nd, or a mixture thereof, and a=0.001~2.0,
b=0~4.5,
c=0.01~8.0,
d=0.01~22.0,
e=0.01~0.7,
f=0.01~8.0,
g=0.01~6.0,
h=8~16, and
x=number of oxygen atoms required to satisfy the valence requirement of the other elements present, and b) a silica carrier

14 Claims, No Drawings

FLUIDIZED-BED CATALYST FOR PROPYLENE AMMOXIDATION TO ACRYLONITRILE

BACKGROUND OF THE INVENTION

1.1. Field Of The Invention

The present invention relates to an ammoxidation catalyst, in particular, to a fluidized-bed catalyst for ammoxidation of propylene to acrylonitrile.

1.2. Background Art

Over the decades, multi-component molybdenum/bismuth catalysts have been widely used in the propylene ammoxidation process to produce acrylonitrile. In order to further increase the efficiency of such a process, attempts have been made to improve the performance of the multi-component Mo/Bi catalysts.

U.S. Pat. No. 4,443,556 discloses a catalyst of a Mo—Bi—Fe—Na—P system. In the patent, the catalyst was evaluated in a fixed bed under atmospheric pressure, thus can not reflect its performance in a fluidized-bed under increased pressure.

U.S. Pat. No. 4,978,765 discloses a catalyst comprising molybdenum/bismuth/iron/antimony/nickel/alkali metal(s) without additional metal elements. The catalyst was evaluated under atmospheric pressure.

U.S. Pat.No. 5,212,137 discloses a catalyst of a Fe—Bi—Mo—Ni—Mg—Cs—K system, with an optional element selected from Co, Mn, Cr, P, Sb, Te, Na, Ce, or W, wherein sodium is not an essential element. Moreover, the results are obtained in a fixed bed.

Nowadays, however, acrylonitrile manufacturers are paying more attention to increasing the acrylonitrile output of existing plants rather than setting up new plants for economic reasons, thus requiring a catalyst capable of affording high acrylonitrile yields under increased pressure. Such a catalyst is also expected to be suitable for fluidized-bed operations which are employed in most propylene ammoxidation plants.

U.S. Pat. No. 5,134,105 discloses a catalyst of a Mo—Bi—Fe—Co—Ni—Cr system, with optional elements selected from rare earth elements and alkali metals; however, no description was made with respect to specific rare earth elements and sodium throughout the specification. The catalyst gives a once-through acrylonitrile yield of up to 80.2%

U.S. Pat. No. 5,235,088 discloses a catalyst of a Mo—Bi—Fe—Co—Ni—Cr system with additional elements selected from P and/or Sb, alkali metals, and alkaline earth metals, rare earth metals, Nb, Tl, As, Mg, Zn, Cd, V, B, Ca, Sn, Ge, Mn, W and/or Te. Such a catalyst achieves a once-through acrylonitrile yield of up to 80.2%.

U.S. Pat. No. 5,223,469 by the present inventors discloses a catalyst of a Ni—Co—Na—Fe—Bi—Mo system with certain additional elements. The catalyst affords a once-through acrylonitrile yield of up to 81.9%.

Based upon U.S. Pat. No. 5,223,469, the present inventors have made further investigations and have found out that the multi-component Mo/Bi catalyst can be further improved in the connection of fluidized-bed propylene ammoxidation process under increased pressure by introduction of several specific metals and combinations thereof with Co and/or Ni, thus completing the invention.

SUMMARY OF THE INVENTION

Accordingly, an object of the invention is to provide a fluidized-bed catalyst for propylene ammoxidation to acrylonitrile, which achieves high performance in a fluidized-bed reaction under increased pressure, and comprises a) a catalytic composition represented by the following general formula:

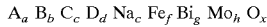

wherein

A represents K, Rb, Cs, Tl, or a mixture thereof,

B represents Mn, Mg, Sr, Ca, Ba, or a mixture thereof,

C represents P, As, B, Sb, Cr, W, V, or a mixture thereof, and

D represents one of the following groups:
1) Ni alone,
2) Co alone,
3) Ni and one selected from Li, Pr, Nd, or a mixture thereof,
4) Co and one selected from Li, Pr, Nd, or a mixture thereof,
5) Ni, Co and one selected from Li, Pr, Nd, or a mixture thereof, and a=0.001~2.0,
b=0~4.5,
c=0.01~8.0,
d=0.01~22.0,
e=0.01~0.7,
f=0.01~8.0,
g=0.01~6.0,
h=8~16, and =number of oxygen atoms required to satisfy the valence requirement of the other elements present, and b) a silica carrier

DETAILED DESCRIPTION OF THE INVENTION

The present invention provides a fluidized-bed catalyst for ammoxidation of propylene to acrylonitrile, comprising a) a catalytic composition represented by the following general formula:

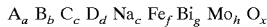

wherein

A represents K, Rb, Cs, Tl, or a mixture thereof,

B represents Mn, Mg, Sr, Ca, Ba, or a mixture thereof,

C represents P, As, B, Sb, Cr, W, V, or a mixture thereof, and

D represents one of the following groups:
1) Ni alone,
2) Co alone,
3) Ni and one selected from Li, Pr, Nd, or a mixture thereof,
4) Co and one selected from Li, Pr, Nd, or a mixture thereof,
5) Ni, Co and one selected from Li, Pr, Nd, or a mixture thereof, and a=0.001~2.0,
b=0~4.5,
c=0.01~8.0,
d=0.01~22.0,
e=0.01~0.7,
f=0.01~8.0, g=0.01~6.0, h=8~16, and x=number of oxygen atoms required to satisfy the valence requirement of the other elements present, and b) a silica carrier.

The catalyst according to the invention comprises a catalytic composition and a silica carrier. The content of silica carrier is 30–70%, and preferably 40–60% by weight of the total weight of the catalyst.

Of the elements represented by A, one or more elements can be present in the catalyst of the invention, which also applies to the other elements represented by B and C.

Compared to the catalyst disclosed by the present inventors in U.S. Pat. No. 5,223,469, the major improvement of the catalyst of the current invention resides in, inter alia, the introduction of Li, Pr and/or Nd and combination thereof with Co and/or Ni.

According to a preferred embodiment of the invention, the atomic ratios of the elements of the catalytic composition are as follows:

a=0.01~1.0, b=0.05~2.0, c=0.4~4.0, d=0.5~20.0, e=0.2~0.5, f=0.4~4.0, g=0.1~4.0, and h=12~14, Another preferred embodiment of the invention describes a catalyst wherein D represents Ni and/or Co, and Pr and/or Nd, and d=0.01~20.0, preferably 1.0~10.0. In the catalyst, the atomic ratio of Co and/or Ni to Pr and/or Nd is 3~15:1, and preferably 5~13:1, while the atomic ratios of Co to Ni, and of Pr to Nd are not critical.

A further preferred embodiment of the invention describes a catalyst wherein D represents Li, Ni and Co, b=0.01~3.0, and preferably 0.5~2.0, and d=0.01~20.0, and preferably 1.0~13.0. The atomic ratio of Li to Ni and Co is preferably 0.005~01, and the atomic ratio of Ni to Co is 0.1~3.0, and preferably 0.1~1.0. Within the range of the atomic ratios indicated above, the catalyst displays good performance.

A still further preferred embodiment of the invention describes a catalyst wherein D represents Ni, and d =0.5~9.0. It is unexpectedly found that in the present invention the absence of Co from the catalyst does not much affect its performance. This is a significant finding, because the cost of the catalyst can be lowered by excluding cobalt, an expensive element, from the catalyst without decreasing the performance of the catalyst. Without being bound by any theory, it is believed, based upon our findings, that among molybdates of Co, Ni, Mn and Mg, cobalt molybdate displays the highest activity in the propylene ammoxidation process, favoring formation of carbon dioxide. Therefore, it follows that the absence of cobalt from the catalyst leads to an increase of the selectivity to acrylonitrile.

The catalyst provided by the invention achieves high once-through acrylonitrile yields in the fluidized-bed propylene ammoxidation process even under increased pressure, thus making possible the increase of the output of the existing acrylonitrile plant without additional equipment cost.

The catalyst of the invention may be prepared by any conventional process for preparing a catalyst of the same kind. For example, methods such as co-precipitating the various ingredients in water, or alternatively mixing the catalyst components with the carrier in water, followed by spray-drying and calcining, may be used.

To introduce the element represented by A into the catalyst, one can employ nitrate, hydroxide and salts thereof capable of yielding the corresponding oxide upon calcination.

To introduce the element represented by B into the catalyst, one can employ oxide thereof or its salts capable of yielding its oxide upon calcination.

To introduce P, As or B into the catalyst, one preferably employs acid thereof or its ammonium salts. For Cr, it is preferred to employ chromium trioxide, chromium nitrate or mixture thereof. For antimony, it is preferred to employ $Sb_2O_3$, $Sb_2O_5$, or antimony halogenide and antimony sol capable of hydrolyzing to antimony oxide. For tungsten, one can employ tungsten oxide or ammonium tungstate, and for vanadium, one can employ ammonium meta-vanadate.

To introduce sodium into the catalyst, one can employ nitrate, hydroxide, silicate or any other compounds thereof that can decompose to yield $Na_2O$.

To introduce Ni, Co, Pr, Nd, Fe and Bi into the catalyst, one can employ their oxides or salts, preferably water soluble nitrates, capable of decomposing to give their oxides.

To introduce Mo, one can employ molybdenum oxide or ammonium molybdate.

Silica sol can be preferably used as silica carrier, for example, an $NH_3$-stabilized Na-free silica sol with a silica content of 40% by weight. To facilitate the preparation of the catalyst, it is sometimes desired that the sodium component is pre-added into the $NH_3$-stabilized silica sol; however, the sodium content of the catalyst is preferably no less than 1000 ppm when the silica content is 40% by weight.

To prepare the catalyst, one can first mix various catalyst components, supporting materials and water to form a slurry. Then heat-treat the slurry at a temperature of 50°–120°C. for at least 10 minutes, followed by spray-drying to produce spherical particles, and finally calcine the particles to give a catalyst. For a spray-drying operation, one can employ a pressure nozzle, double-stream spray-dryer, or a centrifugal rotating-disc, which is most preferable, in order to obtain a good distribution range of particle size.

The calcination of the catalyst is achieved in two stages. First, the catalyst is heated at a temperature of 200°–400°C. for 0.5–2 hours to decompose the salts of various elements, followed by a temperature of 450°–800°C., preferably 500°–650°C. to calcine the catalyst. The two stages can be run separately, or continuously, while an air stream passes over the catalyst.

The fluidized-bed propylene ammoxidation process to acrylonitrile with the use of the present catalyst may be carried out with the same process parameters as used conventionally. Namely, it may be effected by feeding propylene, ammonia and oxygen to a reactor loaded with the fluidized-bed catalyst of the invention. Although the saturated hydrocarbons have little effect on the reaction, the propylene content in the feed materials is preferably at least 85% by mole from an economic point of view. As an ammonia source preferably used is a fertilizer-grade liquid ammonia. As an oxygen source, one can use pure oxygen or oxygen-enriched air, with the latter preferable for economic reasons.

The molar ratio of the oxygen to propylene in the feed gas can be varied in a range between 0.8:1 and 10:1, preferably between 1.0:1 and 1:3:1. The actual molar ratio of air to propylene is preferably between 8:1 and 10:1. Such a low ratio constitutes an advantage of the catalyst of the present invention. As a matter of course, the ratio can be raised to 11:1, if desired, without adverse effect on the reaction. However, from safety consideration, oxygen in the reaction gas is no more than 7% by volume, preferably no more than 4%.

When the catalyst of the present invention is used in a fluidized-bed reactor, the reaction temperature is in the range of 420°–490°C., preferably in the range of 440°–460°C., and the pressure is usually in the range of 0.01–0.2 Mpa, preferably in the range of 0.04–0.2 Mpa.

The weight of propylene feed per unit weight of catalyst per hour (WWH) is in the range of 0.04–0.20, preferably in the range of 0.05–0.10.

The definition of WWH is

WWH=weight of propylene feed/weight of catalyst. hr. The technology for recovery and refining of acrylonitrile which is produced using the present catalyst is the same as the conventional one. The unreacted ammonia in the effluent from the fluidized-bed reactor is removed in a neutralization tower and all the organic components are absorbed by water in an absorption tower. Extractive distillation is used for removing hydrogen cyanide and water from the absorbed liquid to obtain highly purified acrylonitrile.

DESCRIPTION OF PREFERRED EMBODIMENTS

The present invention will be further described in more detail with reference to the following examples, wherein the propylene conversion, acrylonitrile selectivity and once-through acrylonitrile yield are defined as follows.

propylene conversion (%) =

$$\frac{\text{moles of propylene converted}}{\text{moles of propylene fed}} \times 100$$

acrylonitrile selectivity (%) =

$$\frac{\text{moles of acrylonitrile produced}}{\text{moles of propylene converted}} \times 100$$

once-through acrylonitrile yield (%) =

$$\frac{\text{moles of acrylonitrile produced}}{\text{moles of propylene fed}} \times 100$$

Example 1

A material (I) was prepared by mixing 20 percent by weight potassium nitrate solution 9.0g, 20 percent by weight rubidium nitrate solution 17.0 g, 20 percent by weight cesium nitrate solution 7.0 g, and 20 percent by weight sodium nitrate solution 18.5 g.

A material (II) was prepared by dissolving 19.7 g ammonium tungstate in 100 ml of 5 percent by weight ammonia water followed by mixing with a solution of 374.7 g ammonium 10 molybdate in 300 ml water of a temperature ranging 500°–95°C.

A material (III). was prepared by dissolving a mixture of 78.1 g bismuth nitrate, 51.9 g manganese nitrate, 149.3 g iron nitrate, 63.9 g cobalt nitrate, 215.0 g nickel nitrate, 4.4 g chromium nitrate, and 23.9 g praseodymium nitrate in 15 70 ml water by heating.

Material (I) was mixed with 40 percent by weight ammonia-stabilized sodium-free silica sol 1250 g, to which 85 percent by weight phosphoric acid 4.2 g, materials (II) and (III) were added while stirring. After thoroughly stirring, a paste was formed, which was spray dried according to a conventional method to obtain microspheres, followed by calcining at 670°C. for 1 hour in a rotating oven with an inner-diameter of 89 mm and a length of 1700 mm ($\phi$89× 1700 mm). The prepared catalyst had an composition as follows:

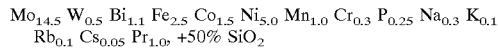

$Mo_{14.5} W_{0.5} Bi_{1.1} Fe_{2.5} Co_{1.5} Ni_{5.0} Mn_{1.0} Cr_{0.3} P_{0.25} Na_{0.3} K_{0.1} Rb_{0.1} Cs_{0.05} Pr_{1.0}, +50\% SiO_2$

The catalyst was evaluated in a fluidized-bed reactor having an inner-diameter of 38 mm. The reaction temperature was 435 OC, the pressure 0.08 Mpa, the molar ratio of propylene:ammonia:air=1:1.2:9.8, and the WWH 0.045. The results were:

propylene conversion 98.5%, acrylonitrile selectivity 83.7%, and once-through acrylonitrile yield 82.4%.

When the feeding rate of propylene at the above mentioned ratio was 245 ml/mm, the amount of acrylonitrile produced was $$(245/22.4)\times 0.824\times 53=477.7 \text{ mg/mm}.$$

when the molar ratio of the raw materials was changed to propylene: ammonia: air=1:1.5:10.5 with other operation parameters unchanged, the evaluation results were:

propylene conversion 98.8%, acrylonitrile selectivity 82.1%, and once-through acrylonitrile yield 81.1%.

When the feeding rate of propylene at this ratio was 219 ml/min, the amount of acrylonitrile produced was $$(219/22.4)\times 0.811\times 53=420.2 \text{ mg/min}$$

Example 2

The catalyst was prepared by the process as described in Example 1. Material (I) was prepared by mixing a series of percent by weight solutions including 17.0 g rubidium nitrate, 14.5 g cesium nitrate, 13.0 g samarium nitrate, and 19.0 g sodium nitrate, respectively.

Material (II) was prepared by mixing a solution of 40.2 g ammonium tungstate in 300 ml 5 percent by weight ammonia water with another solution of 355.4 g ammonium molybdate in 350 ml water of a temperature ranging 500-95 C.

Material (III) was prepared by mixing 72.3 g bismuth nitrate, 109.5 g iron nitrate, 63.4 g manganese nitrate, 130.2 g cobalt nitrate, 153.3 g nickel nitrate, 6.0 g chromium nitrate, 9.8 g praseodymium nitrate, and 14.9 g neodym nitrate, in 100 ml water.

According to the process described in Example 1, the above materials were mixed with 1000 g 40 percent by weight silica sol and 4.3 g 85 percent by weight phosphoric acid. After shaping and calcining, the catalyst obtained had a composition as follows:

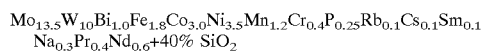

$Mo_{13.5}W_{10}Bi_{1.0}Fe_{1.8}Co_{3.0}Ni_{3.5}Mn_{1.2}Cr_{0.4}P_{0.25}Rb_{0.1}Cs_{0.1}Sm_{0.1} Na_{0.3}Pr_{0.4}Nd_{0.6}+40\% SiO_2$

The evaluation method for catalyst activity was the same as that of Example 1. The operation parameters were also the same as those of Example 1, except the molar ratio of propylene:ammonia:air=1:1.2:9.4. The results were:

propylene conversion 9 8.5%, acrylonitrile selectivity 84.9%, and once-through acrylonitrile yield 83.6%.

Example 3

The catalyst was prepared by the process described in Example 1. Material (I) was prepared by mixing a series of percent by weight solutions including 9.9 g potassium nitrate, 8.0 g cesium nitrate, 22.0 g thallous nitrate, 29.0 g samarium nitrate and 21.0 g sodium nitrate, respectively.

Material (II) was prepared by mixing a solution of 26.9g ammonium tungstate in 50 ml 5 percent by weight ammonia water with another solution of 346.4 g ammonium molybdate in 300 ml water of a temperature ranging 50°–95 ° C.

Material (III) was prepared by mixing 64.5 g bismuth nitrate, 149.3 g iron nitrate, 193.6 g cobalt nitrate, 112.4 g nickel nitrate, 58.9 g manganese nitrate, 6.7 g chromium nitrate, and 13.6 g praseodymium nitrate in 70 ml water.

According to the process described in Example 1, the above materials were mixed with 1250 g 40 percent by weight 25 silica sol and 2.9 g 85 percent by weight phosphoric acid. After shaping and calcining, the catalyst obtained had a composition as follows:

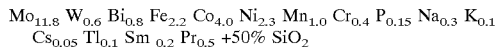

$Mo_{11.8} W_{0.6} Bi_{0.8} Fe_{2.2} Co_{4.0} Ni_{2.3} Mn_{1.0} Cr_{0.4} P_{0.15} Na_{0.3} K_{0.1} Cs_{0.05} Tl_{0.1} Sm_{0.2} Pr_{0.5} +50\% SiO_2$

The evaluation method for catalyst activity was the same as that of Example 1. The operation parameters were also the same as those of Example 1, except the molar ratio of propylene:ammonia:air=1:1:8.9. The results were:

propylene conversion 97.4%, acrylonitrile selectivity 83.1%, and once-through acrylonitrile yield 80.9%.

Example 4

The catalyst was prepared by the process described in Example 1. Material (I) was prepared by mixing a series of 20 percent by weight solutions including 9.0 g cesium nitrate, 15.5 g samarium nitrate, 24.0 g thallous nitrate, and 23.0 g sodium nitrate, respectively.

Material (II) was prepared by mixing a solution of 24.4 g ammonium tungstate in 100 ml 5 percent by weight ammonia water with another solution of 366.4 g ammonium molybdate in 300 ml water of a temperature ranging 50°–95 ° C.

Material (III) was prepared by mixing 78.8 g bismuth nitrate, 132.6 g iron nitrate, 76.7 g manganese nitrate, 92.6 g magnesium nitrate, 105.1 g cobalt nitrate, 122.0 g nickel nitrate, 7.3 g chromium nitrate, and 15.0 g neodym nitrate in 70 ml water.

According to process described in Example 1, the above materials were mixed with 1250 g 40 percent by weight silica sol. After shaping and calcining, the catalyst obtained had a composition as follows:

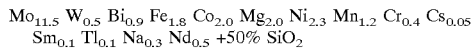

$Mo_{11.5} W_{0.5} Bi_{0.9} Fe_{1.8} Co_{2.0} Mg_{2.0} Ni_{2.3} Mn_{1.2} Cr_{0.4} Cs_{0.05} Sm_{0.1} Tl_{0.1} Na_{0.3} Nd_{0.5} +50\% SiO_2$

The evaluation method for catalyst activity was the same as that of Example 1. The operation parameters were also the same as those of Example 1, except the molar ratio of propylene:ammonia:air=1:1.15:9.5. The results were:

propylene conversion 96.7%, acrylonitrile selectivity 82.8%, and once-through acrylonitrile yield 80.1%.

Example 5

The catalyst was prepared by the process described in Example 1. Material (I) was prepared by mixing a series of 20 percent by weight solutions including 20.5 g sodium nitrate, 19.8 g potassium nitrate and 8.0 g cesium nitrate, respectively.

Material (II) was prepared by dissolving 11.2 g ammonium metavanadate and 348.9 g ammonium molybdate in 300 ml water of a temperature ranging 50°–95 ° C.

Material (III) was prepared by mixing 77.3 g bismuth nitrate, 130.1 g iron nitrate, 234.1 g nickel nitrate, 67.1 g strontium nitrate, 56.5 g manganese nitrate, 4.8 g chromium..nitrate, 13.0 g praseodymium nitrate, and 26.6 g neodym nitrate, in 100 ml water.

According to the process described in Example 1, the above materials were mixed with 1250 g 40 percent by weight silica sol. After shaping and calcining, the catalyst obtained had a composition as follows:

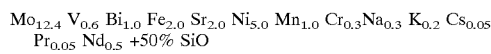

$Mo_{12.4} V_{0.6} Bi_{1.0} Fe_{2.0} Sr_{2.0} Ni_{5.0} Mn_{1.0} Cr_{0.3} Na_{0.3} K_{0.2} Cs_{0.05} Pr_{0.05} Nd_{0.5} +50\% SiO$

The catalyst evaluation method was the same as that of Example 1. The operation parameters were also the same as those of Example 1, except the molar ratio of propylene:ammonia:air=1:1.1:9.4 The results were:

propylene conversion 97.8%, acrylonitrile selectivity 82.8%, and once-through acrylonitrile yield 81.0%.

Example 6

The catalyst was prepared by the process described in Example 1. Material (I) was prepared by mixing a series of 20 percent by weight solutions including 21.5 g sodium nitrate, 9.9 g potassium nitrate, 19.5 g rubidium nitrate, 8.0 g cesium nitrate and 14.5 g samarium nitrate, respectively.

Material (II) is prepared by mixing 81.9 g bismuth nitrate, 124.0 g iron nitrate, 14.2 g calcium nitrate, 245.5 g cobalt nitrate, 98.6 g nickel nitrate, 89.7 g manganese nitrate, 5.1 chromium nitrate, and 11.0 g praseodymium nitrate in 80 ml water.

Material (III) was prepared by dissolving 312.8 g ammonium molybdate, 54.6 g ammonium tungstate, and 5.9 g ammonium metavanadate in 300 ml 5 percent by weight ammonia water of a temperature ranging 50°–95° C.

According to the process described in Example 1, the above materials were mixed with 1250 g 40 percent by weight silica sol. After shaping and calcining, the catalyst obtained had a composition as follows:

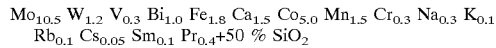

$Mo_{10.5} W_{1.2} V_{0.3} Bi_{1.0} Fe_{1.8} Ca_{1.5} Co_{5.0} Mn_{1.5} Cr_{0.3} Na_{0.3} K_{0.1} Rb_{0.1} Cs_{0.05} Sm_{0.1} Pr_{0.4} +50 \% SiO_2$

The evaluation method for catalyst activity was the same as that of Example 1. The operation parameters were also the same as those of Example 1, except the molar ratio of propylene: ammonia: air=1:1.15:9.1. The results were:

propylene conversion 97.2%, acrylonitrile selectivity 83.7%, and once-through acrylonitrile yield 81.4%.

Example 7

A material (I) was prepared by mixing a series of 20 percent by weight solutions including 10.8 g potassium nitrate, 62.0 g rubidium nitrate, 8.5 g cesium nitrate, 23.0 g sodium nitrate and 3.0 g lithium nitrate, respectively.

A material (II) was prepared by dissolving 58.4 g ammonium tungstate in 100 ml 5 percent by weight ammonia water followed by mixing with a solution of 343.7 g ammonium molybdate in 300 ml water of a temperature ranging 50°–95° C.

A material (III) was prepared by dissolving a mixture of 70.0 g bismuth nitrate, 63.9 g manganese nitrate, 132.4 g iron nitrate, 183.6 g cobalt nitrate, 148.3 g nickel nitrate, and 7.3 g chromium nitrate in 70 ml water by heating.

Material (I) was mixed with 40 percent by weight ammonia-stabilized sodium-free silica sol 1250 g, to which 85 percent by weight phosphoric acid 5.1 g, materials (II) and (III) were added while stirring. After thoroughly stirring, a paste was formed, which was spray-dried according to a conventional method to obtain microspheres, followed by calcining at 670° C. for 1 hour in a rotating oven with an inner-diameter of 89 mm and a length of 1700 mm (φ89× 1700 mm). The prepared catalyst had a composition as follows:

$$Mo_{10.8} W_{1.2} Bi_{0.8} Fe_{1.8} Co_{3.5} Ni_{2.8} Mn_{1.0} Cr_{0.4} P_{0.25} Na_{0.3} Li_{0.05} K_{0.1} Rb_{0.3} Cs_{0.05} +50\% SiO_2$$

The catalyst was evaluated in a fluidized-bed reactor having an inner-diameter of 38 mm. The reaction temperature was 435° C., the pressure 0.08 MPa, the molar ratio of propylene:ammonia: air=1:1.2:9.2, and the WWH 0.045. The results were:

propylene conversion 96.2%, acrylonitrile selectivity 85.5%, and once-through acrylonitrile yield 82.2%.

When the feeding rate of propylene at the above-mentioned ratio was 245 ml/min, the amount of acrylonitrile produced was (245/22.4)×0.822 ×53=476.5 mg/min.

When the molar ratio of the raw materials was changed to propylene:ammonia:air=1:1.5:10.5 with other operation parameters unchanged, the evaluation results were:

propylene conversion 97.8%, acrylonitrile selectivity 83.1%, and once-through acrylonitrile yield 81.3%.

When the feeding rate of propylene at this ratio was 219 ml/min, the amount of acrylonitrile produced was (219/22.4)×0.813×53=420.9 mg/min

Example 8

The catalyst was prepared by the process described in Example 7. Material (I) was prepared by mixing a series of 20 percent by weight solutions including 9.0 g rubidium nitrate, 12.0 g cesium nitrate, 6.5 g samarium nitrate, 19.5 g sodium nitrate and 16.0 g lithium nitrate, respectively.

Material (II) was prepared by mixing a solution of 20.9 g ammonium tungstate in 300 ml 5 percent by weight ammonia water with another solution of 388.2 g ammonium molybdate in 350 ml water of a temperature ranging 50°–95°C.

Material (III) was prepared by mixing 90.1 g bismuth nitrate, 113.8 g iron nitrate, 54.9 g manganese nitrate, 180.3 g cobalt nitrate, 42.4 g strontium nitrate, 45.5 g nickel nitrate and 4.7 chromium nitrate, in 100 ml water.

According to the process described in Example 7, the above materials were mixed with 1000 g 40 percent by weight silica sol and 8.8 g 85 percent by weight phosphoric acid. After shaping and calcining, the catalyst obtained had a composition as follows:

$$Mo_{14.2} W_{0.5} Bi_{1.2} Fe_{1.8} Sr_{1.3} Co_{4.0} Ni_{1.0} Mn_{1.0} Cr_{0.3} P_{0.5} Rb_{0.05} Cs_{0.1} Sm_{0.05} Na_{0.3} Li_{0.3} +40\% SiO_2$$

The evaluation method for catalyst activity was the same as that of Example 7. The operation parameters were also the same as those of Example 7, except the molar ratio of propylene:ammonia:air=1:1.2:9.4. The results were:

propylene conversion 98.5%, acrylonitrile selectivity 85.0%, and once-through acrylonitrile yield 83.7%.

Example 9

The catalyst was prepared by the process described in Example 7. Material (I) was prepared by mixing a series of 20 percent by weight solutions including 11.0 g potassium nitrate, 27.0 g lithium nitrate, 10.5 g thallous nitrate and 20.0 g sodium nitrate, respectively.

Material (II) was prepared by mixing a solution of 42.5 g ammonium tungstate and 3.7 g ammonium metavanadate in 50 ml 5 percent by weight ammonia water with a solution of 356.0 g ammonium molybdate in 300 ml water of a temperature 15 ranging 50°–95° C.

Material (III) was prepared by mixing 76.4 g bismuth nitrate, 160.8 g iron nitrate, 91.7 g cobalt nitrate, 162.0 g nickel nitrate, 8.8 calcium nitrate, 83.7 g manganese nitrate, and 6.4 g chromium nitrate in 70 ml water.

According to the process described in Example 7, the above materials were mixed with 1250 g 40 percent by weight silica sol, 2.7 g 85 percent by weight phosphoric acid, and a solution of 9.7 g boric acid in 10 ml water. After shaping and calcining, the catalyst obtained had a composition as follows:

$$Mo_{12.8} W_{1.0} V_{0.2} Bi_{1.0} Fe_{2.5} Ca_{1.0} Ni_{3.5} Co_{2.0} Mn_{1.5} Cr_{0.4} P_{0.15} B_{1.0} Na_{0.3} Li_{0.5} K_{0.1} Tl_{0.05} +50\% SiO_2$$

The evaluation method for catalyst activity was the same as that of Example 7. The operation parameters were also the same as those of Example 7, except the molar ratio of propylene:ammonia:air=1:1:8.9. The results were:

propylene conversion 96.8%, acrylonitrile selectivity 83.9%, and once-through acrylonitrile yield 81.2%.

Example 10

The catalyst was prepared by the process described in Example 7. Material (I) was prepared by mixing a series of 20 percent by weight solutions including 8.5 g cesium nitrate, 15.0 g samarium nitrate, 23.5 g thallous nitrate, 22.5 g sodium nitrate and 18.0 g lithium nitrate, respectively.

Material (II) was prepared by mixing a solution of 93.9 g ammonium tungstate and 10.2 g ammonium metavanadate in 100 ml 5 percent by weight ammonia water with another solution of 291.8 g ammonium molybdate in 300 ml water of a temperature ranging 50°–95° C.

Material (III) was prepared by mixing 84.4 g bismuth nitrate, 142.0 g iron nitrate, 61.6 g manganese nitrate, 44.6 g magnesium nitrate, 202.5 g cobalt nitrate, 102.2 g nickel nitrate, and 3.6 g chromium nitrate in 70 ml water.

According to the process described in Example 7, the above materials were mixed with 1250 g 40 percent by weight silica sol. After shaping and calcining, the catalyst obtained had a composition as follows:

$$Mo_{9.5} W_{2.0} V_{0.5} Bi_{1.0} Fe_{2.0} Mg_{1.0} Co_{4.0} Ni_{2.0} Mn_{1.0} Cr_{0.2} Cs_{0.1}$$

$Sm_{0.1} Tl_{0.1} Na_{0.3} + 50\% SiO_2$

The evaluation method for catalyst activity was the same as that of Example 7. The operation parameters were also the same as those of Example 7, except the molar ratio of propylene:ammonia:air=1:1.15:9.5. The results were:
 propylene conversion 97.1%,
 acrylonitrile selectivity 83.3%, and
 once-through acrylonitrile yield 80.9%.

Example 11

The catalyst was prepared by the process described in Example 7. Material (I) was prepared by mixing a series of 20 percent by weight solutions including 21.5 g sodium nitrate, 20.7 g potassium nitrate, 16.5 g cesium nitrate, 14.5 g rubidium nitrate and 8.5 g lithium nitrate, respectively.

Material(II) was prepared by dissolving 9.1 g ammonium tungstate and 379.6 g ammonium molybdate in 300 ml water of a temperature ranging 50°–95° C.

Material(III) was prepared by mixing 73.3 g bismuth nitrate, 123.4 g iron nitrate, 109.4 g cerous nitrate, 171.1 g cobalt nitrate, 29.8 g manganese nitrate, 5.1 g chromium nitrate, and 98.7 g nickel nitrate in 100 ml water.

According to the process described in Example 7, the above materials were mixed with 1250 g 40 percent by weight silica sol. After shaping and calcining, the catalyst obtained had a composition as follows:

$Mo_{12.8} W_{0.2} Bi_{0.9} Fe_{1.8} Ce_{1.5} Co_{3.5} Ni_{2.0} Mn_{0.5} Cr_{0.3} Na_{0.3} Li_{0.15} K_{0.2} Cs_{0.1} Rb_{0.15} + 50\% SiO_2$

The catalyst evaluation method was the same as that of Example 1. The operation parameters were also the same as those of Example 7, except the molar ratio of propylene:ammonia:air=1:1.1:9.4. The results were:
 propylene conversion 97.8%,
 acrylonitrile selectivity 82.2%, and
 once-through acrylonitrile yield 80.4%.

Example 12

The catalyst was prepared by the process described in Example 7. Material (I) was prepared by mixing a series of 20 percent by weight solutions including 21.5 g sodium nitrate, 10.8 g potassium nitrate, 14.5 g samarium nitrate, 5.0 g cesium nitrate, 11.5 g lithium nitrate and 11.5 g thallous nitrate, respectively.

Material(II) was prepared by mixing 82.1g bismuth nitrate, 138.2 g iron nitrate, 93.1 g lanthanum nitrate, 147.8 g cobalt nitrate, 149.2 g nickel nitrate, 60.0 g manganese nitrate, and 13.7 g chromium nitrate in 80 ml water.

Material(III) was prepared by dissolving 298.9 g ammonium molybdate and 54.8 g ammonium tungstate in 300 ml 5 percent by weight ammonia water of a temperature ranging 50°–95°C.

According to the process described in Example 7, the above materials were mixed with 1250 g 40 percent by weight silica sol. After shaping and calcining, the catalyst obtained had a composition as follows: $Mo_{10.0} W_{1.2} Cr_{0.8} Bi_{1.0} Fe_{2.0} La_{1.5} Co_{3.0} Ni_{3.0} Mn_{1.0} Na_{0.3} Li_{0.2} K_{0.1} Cs_{0.03} Tl_{0.05} Sm_{0.1} + 50\% SiO_2$ The evaluation method for catalyst activity was the same as that of Example 7. The operation parameters were also the same as those of Example 7, except the molar ratio of propylene:ammonia:air=1:1.15:9.1. The results were:
 propylene conversion 97.6%,
 acrylonitrile selectivity 84.4%, and
 once-through acrylonitrile yield 82.4%.

Example 13

A material (I) was prepared by mixing a series of 20 percent by weight solutions including 11.1 g potassium nitrate, 10.5 g rubidium nitrate, 8.8 g cesium nitrate, and 23.0 g sodium nitrate, respectively.

Material(II) was prepared by dissolving 39.3 g ammonium tungstate in 100 ml 5 percent by-weight ammonia water followed by mixing with a solution of 359.9 g ammonium molybdate in 300 ml water of a temperature of 50°–95° C.

Material(III) was prepared by dissolving a mixture of 88.3 g bismuth nitrate, 129.0 g manganese nitrate, 126.3 g iron nitrate, 283.4 g nickel nitrate, and 7.4 g chromium nitrate in 70 ml water by heating.

Material(I) was mixed with 40 percent by weight ammonia- stabilized sodium-free silica sol 1250 g, to which 85 percent by weight phosphoric acid 3.1 g, materials (II) and (III) were added while stirring. After thoroughly stirring, a paste was formed, which was spray-dried according to a conventional method to obtain microspheres followed by calcining at 670 OC for 1 hour in a rotating oven with an inner-diameter of 89 mm and a length of 1700 mm ($\phi 89 \times 1700$ mm). The prepared catalyst had a composition as follows:

$Mo_{11.2} W_{0.8} Bi_{1.0} Fe_{1.7} Ni_{5.3} Mn_{2.0} Cr_{0.4} P_{0.15} Na_{0.3} K_{0.1} Rb_{0.1} Cs_{0.05} + 50\% SiO_2$

The catalyst was evaluated in a fluidized-bed reactor having an inner-diameter of 38 mm. The reaction temperature was 435 OC, the pressure 0.08 Mpa, the molar ratio of propylene:ammonia:air=1:1.2:9.2, and the WWH 0.045. The results were:
 propylene conversion 96.2%,
 acrylonitrile selectivity 84.4%, and
 once-through acrylonitrile yield 81.2%.

When the feeding rate of propylene at the above mentioned ratio was 245 ml/min, the amount of acrylonitrile produced was $(245/22.4) \times 0.812 \times 53 = 470.7$ mg/min.

When the molar ratio of the raw materials was changed to propylene:ammonia:air=1:1.5:10.5 with other operation parameters unchanged, the evaluation results were:
 propylene conversion 97.8%,
 acrylonitrile selectivity 82.1%, and
 once-through acrylonitrile yield 80.3%.

When the feeding rate of propylene at this ratio was 219 ml/min, the amount of acrylonitrile produced was $(219/22.4) \times 0.803 \times 53 = 415.7$ mg/min.

Example 14

The catalyst was prepared by the process described in Example 13. Material (I) was prepared by mixing a series of 20 percent by weight solutions including 9.5 g rubidium nitrate, 15.5 g cesium nitrate, 14.0 g samarium nitrate, and 20.5 g sodium nitrate, respectively Material(II) was prepared by mixing a solution of 21.7 g ammonium tungstate in 300 ml 5 percent by weight ammonia water with another solution of 398.3 g ammonium molybdate in 350 ml water of a temperature ranging 50°–95 ° C.

Material(III) was prepared by mixing 70.4 g bismuth nitrate, 131.5 g iron nitrate, 131.3 g manganese nitrate, 236.7 g nickel nitrate, and 6.5 g chromium nitrate in 100 ml water.

According to the process described in Example 13, the above materials were mixed with 1000 g 40 percent by weight silica sol and 4.6 g 85 percent by weight phosphoric acid. After shaping and calcining, the catalyst obtained had a 20 composition as follows:

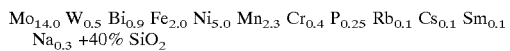
$Mo_{14.0} W_{0.5} Bi_{0.9} Fe_{2.0} Ni_{5.0} Mn_{2.3} Cr_{0.4} P_{0.25} Rb_{0.1} Cs_{0.1} Sm_{0.1} Na_{0.3} +40\% SiO_2$ The evaluation method for catalyst activity was the same as that of Example 13. The operation parameters were also the same as those of Example 13, except the molar ratio of propylene:ammonia:air=1:1.2:9.4. The results were:

propylene conversion 98.5%, acrylonitrile selectivity 84.0%, and once-through acrylonitrile yield 82.7%.

Example 15

The catalyst was prepared by the process described in Example 13. Material (I) was prepared by mixing a series of 20 percent by weight solutions including 10.8 g potassium nitrate, 8.5 g cesium nitrate, 23.5 g thallous nitrate, and 22.5 g sodium nitrate, respectively.

Material (II) was prepared by mixing a solution of 28.4 g ammonium tungstate in 50 ml 5 percent by weight ammonia water with another solution of 365.0 g ammonium molybdate in 300 ml water of a temperature ranging 50°–95° C.

Material (III) was prepared by mixing 59.5 g bismuth nitrate, 128.7 g iron nitrate, 334.6 g nickel nitrate, 62.1 g manganese nitrate, and 7.1 g chromium nitrate in 70 ml water.

According to the process described in Example 13, the above materials were mixed with 1250 g 40 percent by weight silica sol, 3.0 g 85 percent by weight phosphoric acid and a solution of 1.1 g boric acid in 10 ml water. After shaping and calcining, the catalyst obtained had a composition as follows:

$MO_{11.8} W_{0.6} Bi_{0.7} Fe_{1.8} Ni_{6.5} Mn_{1.0} Cr_{0.4} P_{0.15} B_{0.1} Na_{0.3} K_{0.1} Cs_{0.05} Tl_{0.1} +50\% SiO_2$

The evaluation method for catalyst activity was the same as that of Example 13. The operation parameters were also the same as those of Example 13, except the molar ratio of propylene:ammonia:air=1:1:8.9. The results were:

propylene conversion 96.1%, acrylonitrile selectivity 83.7%, and once-through acrylonitrile yield 80.4%.

Example 16

The catalyst was prepared by the process described in Example 13. Material (I) was prepared by mixing a series of 20 percent by weight solutions including 8.0 g cesium nitrate, 14.5 g samarium nitrate, 22.0 g thallous nitrate, and 21.5 g sodium nitrate, respectively.

Material (II) was prepared by mixing a solution of 27.0 g ammonium tungstate in 100 ml 5 percent by weight 35 ammonia water with another solution of 368.1 g ammonium molybdate in 300 ml water of a temperature ranging 50°–95° C.

Material (III) was prepared by mixing 80.9 g bismuth nitrate, 136.2 g iron nitrate, 47.3 g manganese nitrate, 352.8 g nickel nitrate, and 6.7 g chromium nitrate in 70 ml water.

According to the process described in Example 13, the above materials were mixed with 1250 g 40 percent by weight silica sol and 4.8 g 85 percent by weight phosphoric acid.

After shaping and calcining, the catalyst obtained had a composition as follows:

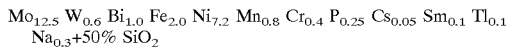
$Mo_{12.5} W_{0.6} Bi_{1.0} Fe_{2.0} Ni_{7.2} Mn_{0.8} Cr_{0.4} P_{0.25} Cs_{0.05} Sm_{0.1} Tl_{0.1} Na_{0.3} +50\% SiO_2$ The evaluation method for catalyst activity was the same as that of Example 13. The operation parameters were also the same as those of Example 13, except the molar ratio of propylene:ammonia:air=1:1.15:9.5. The results were:

propylene conversion 95.5%, acrylonitrile selectivity 83.1%, and once-through acrylonitrile yield 79.4%.

Example 17

The catalyst was prepared by the process described in Example 13. Material (I) was prepared by mixing a series of 20 percent by weight solutions including 19.5 g sodium nitrate, 18.9 g potassium nitrate, and 7.5 g cesium nitrate, respectively.

Material (II) was prepared by dissolving 3.6 g ammonium metavanadate and 382.7 g ammonium molybdate and 16.5 g ammonium tungstate in 300 ml water of a temperature ranging 50°–95° C.

Material (III) was prepared by mixing 81.5 g bismuth nitrate, 124.6 g iron nitrate, 80.4 g strontium nitrate, 201.8 g nickel nitrate, 4.6 g chromium nitrate, and 8.1 g thallium nitrate in 100 ml water.

According to the process described in Example 13, the above materials were mixed with 1250 g 40 percent by weight silica sol and 14.1 g boric acid. After shaping and calcining, the catalyst obtained had a composition as follows:

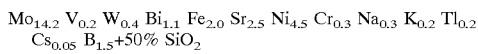
$Mo_{14.2} V_{0.2} W_{0.4} Bi_{1.1} Fe_{2.0} Sr_{2.5} Ni_{4.5} Cr_{0.3} Na_{0.3} K_{0.2} Tl_{0.2} Cs_{0.05} B_{1.5} +50\% SiO_2$ The catalyst evaluation method was the same as that of Example 13. The operation parameters were also the same as those of Example 13, except the molar ratio of propylene:ammonia:air=1:1.1:9.4. The results were:

propylene conversion 97.8%, acrylonitrile selectivity 81.5%, and once-through acrylonitrile yield 79.7%.

Example 18

The catalyst was prepared by the process described in Example 13. Material (I) was prepared by mixing a series of 20 percent by weight solutions including 20.5 g sodium nitrate, 9.9 g potassium nitrate, 18.5 g rubidium nitrate, and 8.0 g cesium nitrate, respectively.

Material (II) is prepared by mixing 78.3 g bismuth nitrate, 131.7 g iron nitrate, 88.6 g lanthanum nitrate, 237.0 g nickel nitrate, 85.7 g manganese nitrate, and 4.9 chromium nitrate in 80 ml water.

Material (III) was prepared by dissolving 327.5 g ammonium molybdate, 52.2 g ammonium tungstate, and 5.7 g ammonium metavanadate in 300 ml 5 percent by weight ammonia water of a temperature ranging 50°–95° C.

According to the process described in Example 13, the above materials were mixed with 1250 g 40 percent by weight silica sol. After shaping and calcining, the catalyst obtained had a composition as follows:

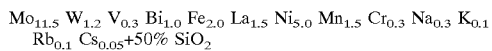

The evaluation method for catalyst activity was the same as that of Example 13. The operation parameters were also the same as those of Example 13, except the molar ratio of propylene:ammonia:air=1:1.15:9.1. The results were:

propylene conversion 94.5%, acrylonitrile selectivity 85.0%, once-through acrylonitrile yield 80.3%.

What is claimed is:

1. A catalyst for ammoxidation of propylene to acrylonitrile, comprising
   a) a catalytic composition represented by the following general formula:

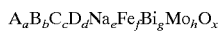

wherein

A represents K, Rb, Cs, Tl, or a mixture thereof,

B represents Mn, Mg, Sr, Ca, Ba, or a mixture thereof,

C represents P, As, B, Sb, Cr, W, V, or a mixture thereof, and

D represents one selected from the following groups:
   1) Ni alone,
   2) Co alone,
   3) Ni and Li, Pr or Nd or a mixture thereof,
   4) Co and Li, Pr or Nd or a mixture thereof.
   5) Ni, Co, and Li, Pr or Nd or a mixture thereof, and $a=0.001\sim 2.0$, $b=0$ to about 4.5, $c=0.01\sim 8.0$, $d=0.01\sim 22.0$, $e=0.01\sim 0.7$, $f=0.01\sim 8.0$, $g=0.01\sim 6.0$, $h=8\sim 16$, and x=number of oxygen atom required to satisfy the valence requirement of the other elements present, and c) a silica carrier.

2. A catalyst of claim 1, wherein b=0.05 to about 2.0.

3. A catalyst of claim 1, wherein D represents Co and/or Ni, and Pr and/or Nd, and d=0.01 to about 20.0.

4. A catalyst of claim 3, wherein d=1.0 to about 10.0.

5. A catalyst of claim 4, wherein the atomic ratio of Co and/or Ni to Pr and/or Nd is 3 to about 15:1.

6. A catalyst of claim 5, wherein the atomic ratio of Co and/or Ni to Pr and/or Nd is 5 to about 13:1.

7. A catalyst of claim 1, wherein D represents Li, Ni and Co, b=0.01~3.0 and d=0.01 to about 20.0.

8. A catalyst of claim 7, wherein b=0.5 to about 2.0 and d=1.0 to about 13.0.

9. A catalyst of claim 8, wherein the atomic ratio of Li to Ni and Co is 0.005 to about 0. 1.

10. A catalyst of claim 9, wherein the atomic ratio between Ni and Co is 0.1 to about 3.0.

11. A catalyst of claim 10, wherein the atomic ratio between Ni and Co is 0.1 to about 1.0.

12. A catalyst of claim 1, wherein D represents Ni and d=0.5 to about 9.0.

13. A catalyst of claim 1, wherein the content of silica carrier is 30 to about 70% by weight of the total weight of the catalyst.

14. A catalyst of claim 13, wherein the content of silica carrier is 40 to about 60% by weight of the total weight of the catalyst.

* * * * *